United States Patent [19]

Carlsson et al.

[11] 4,186,202

[45] Jan. 29, 1980

[54] PHENYL-PYRIDYLAMINE DERIVATIVES

[75] Inventors: Per A. E. Carlsson, Göteborg; Bernt S. E. Carnmalm, Södertälje; Vante B. Ross, Södertälje; Carl B. J. Ulff, Södertälje, all of Sweden

[73] Assignee: Astra Lakemedel Aktiebolag, Södertälje, Sweden

[21] Appl. No.: 773,397

[22] Filed: Mar. 2, 1977

Related U.S. Application Data

[63] Continuation of Ser. No. 632,698, Nov. 17, 1975, abandoned.

[30] Foreign Application Priority Data

Nov. 21, 1974 [SE] Sweden ............................... 7414622

[51] Int. Cl.² ..................... A61K 31/44; C07D 213/38
[52] U.S. Cl. ..................................... 424/263; 546/333
[58] Field of Search ...................... 260/296 R, 295 S; 546/333; 424/263

[56] References Cited

U.S. PATENT DOCUMENTS

| 3,928,369 | 12/1975 | Berntsson et al. | 260/296 R |
| 3,928,613 | 12/1975 | Berntsson et al. | 424/263 |

Primary Examiner—Alan L. Rotman
Attorney, Agent, or Firm—Brumbaugh, Graves, Donohue & Raymond

[57] ABSTRACT

A compound having the formula

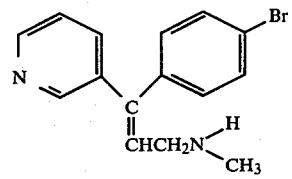

processes for preparing such a compound, intermediates used in the preparation thereof, and pharmaceutical compositions and a method for the treatment of depression and relief of anxiety employing the same.

11 Claims, No Drawings

PHENYL-PYRIDYLAMINE DERIVATIVES

This is a continuation of application Ser. No. 632,698 filed Nov. 17, 1975 now abandoned.

The present invention is related to new compounds having therapeutic activity and to methods for their preparation. The invention is also related to the preparation of pharmaceutical compositions containing at least one of the compounds and to methods for their pharmacological use.

PRIOR ART

Depressive disorders have with more or less success been treated with various compounds.

The antidepressive agents which have received the most widespread, clinical use are the tricyclic tertiary amines imipramine having the structure formula

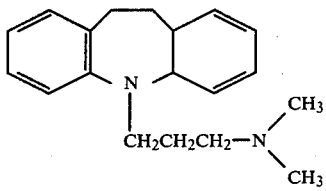

and amitriptyline having the structure formula

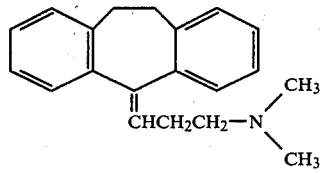

Secondary amines such as desipramine having the structure formula

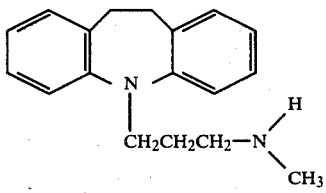

and nortriptyline having the structure formula

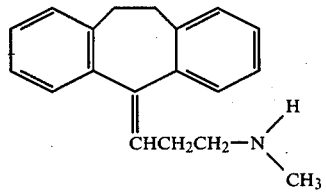

are used to a somewhat less extent. These substances have, however, side effects that are not desired in therapeutic use, such as orthostatism, anticholinergic effects and above all, an arrhythmogenic i.e. heart arrhythmia developing effect when administered in large doses to old patients. Moreover, all the substances mentioned show the drawback that the antidepressive effect does not start until some weeks after treatment. Further, it is known from the literature that certain 1,1-diphenyl-3-aminoprop-1-enes, such as the compound having the formula

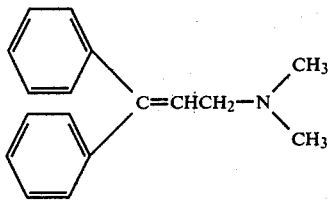

have an antidepressive effect, of J. Med. Chem. 14, 161-4 (1971). Compounds having the formula

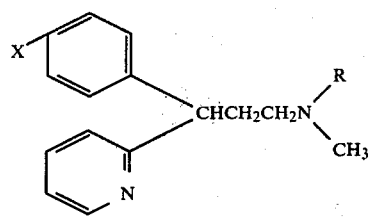

wherein X is chlorine or bromine and R is hydrogen or methyl, are described as having antidepressive effect, cf. U.S. Pat. No. 3,423,510, these compounds however also have a strong antihistaminic effect. From the literature it is also known that a compound having the formula

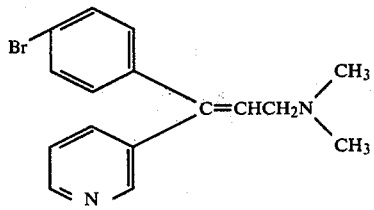

has an antidepressive activity in animal models, cf. Belgian Patent Specification No. 781,105.

In clinical practice different types of depressive disorders are recognized. Depressed patients respond in different ways to the various anti-depressants. Most of these substances inhibit the neuronal uptake of noradrenaline, and some of them additionally inhibit the uptake of 5-hydroxytryptamine. It is believed that inhibition of the uptake of 5-hydroxytryptamine is the mechanism behind a mood elevating property seen in some of these anti-depressants. In addition to the absolute values for inhibition of the uptake of either 5-hydroxytryptamine or noradrenaline the selectivity towards uptake of either of these two amines is of great interest.

OUTLINE OF THE INVENTION

(a) General Outline

A main object of the present invention is to obtain a new compound having a good antidepressive effect. A further object of the invention is to obtain a compound having an antidepressive effect, and giving rise to only minor side-effects, in particular arrhythmogenic effects.

Another object is to obtain compounds having a therapeutic effect against anxiety. Further objects of the invention will be evident from the following description.

The compound of the invention is characterized by the formula

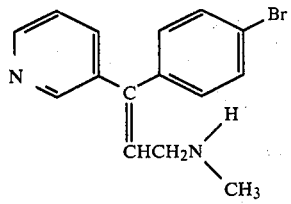

Pharmaceutically acceptable salts of this compound are included within this invention.

Due to the lack of free rotation in the double bond the compound of this invention may exist in different stereoisomeric forms, that is in cis-trans isomers or, according to the IUPAC nomenclature (J. Org. Chem. 35, 2849-2867, September 1970), in an E-form and a Z-form. The compound may be used therapeutically as a mixture of geometrical isomers or in pure E or Z form. The pure geometrical isomers may be prepared from an isomer mixture, from an isomer-pure starting material or directly by a stereoselective synthesis.

The compound of this invention may be administered in the form of a free base or a salt thereof with non-toxic acids. Some typical examples of these salts are the hydrobromide, hydrochloride, phosphate, sulphate, sulphamate, lactate, acetate, citrate, tartrate, malate and maleate.

(b) Pharmaceutical Compositions

In clinical practice the compounds of the present invention will normally be administered orally, rectally or by injection, in the form of pharmaceutical compositions comprising the active ingredient either as a free base or as a pharmaceutically acceptable, non-toxic acid addition salt, e.g. as one of those suggested above in association with a pharmaceutically acceptable carrier. Accordingly, terms relating to the novel compound of this invention are intended to include both the free amine base and the acid addition salts of the free base, unless the context in which such terms are used, e.g. in the specific examples would be inconsistent with the broad concept. The carrier may be a solid, semisolid or liquid diluent, or a capsule. These pharmaceutical compositions constitute a further aspect of this invention. Usually the active substance will constitute from 0.1 to 95% by weight of the composition, more specifically from 0.5 to 20% by weight for compositions intended for injection and from 2 to 50% by weight for compositions suitable for oral administration.

To produce pharmaceuticl compositions containing a compound of the invention in the form of dosage units for oral application, the selected compound may be mixed with a solid pulverulent carrier, e.g. lactose, saccharose, sorbitol, mannitol, starches such as potato starch, corn starch or amylopectin, cellulose derivatives, or gelatine, and a lubricant such as magnesium stearate, calcium stearate or polyethylene glycol waxes, and then compressed to form tablets. If coated tablets are required, the cores, prepared as described above, may be coated with a concentrated sugar solution which may contain, e.g. gum arabic, gelatine, talcum or titanium dioxide. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatine capsules (pearl-shaped closed capsules) consisting of gelatine and, for example, glycerol, or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potato starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions for example, solutions containing from about 0.2% to about 20% by weight of the active substance herein described, the balance being sugar and a mixture of ethanol, water, glycerol, and propyleneglycol. Optionally such liquid preparations may contain coloring agents, flavoring agents, saccharine and carboxymethylcellulose as a thickening agent.

Solutions for parenteral applications by injection can be prepared in an aqueous solution of water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

Suitable daily doses of the compounds of the invention in therapeutic treatment is 25 to 250 mg for peroral administration, preferably 50 to 150 mg and 5 to 50 mg for parenteral administration, preferably 10 to 30 mg. A preparation in dosage unit form for oral administration may contain 10–50 mg, preferably 10 to 25 mg of active substance per dosage unit.

(c) Preferred Embodiment

The preferred isomer of the compound of the invention is the Z-isomer having the structural formula

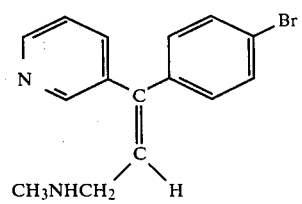

Preferably the compound of the invention will be prepared and used in the form of its salt.

(d) Methods of Preparation

A. Dehydration of a compound of the formula

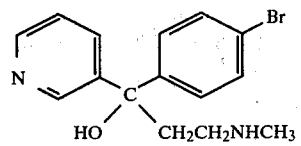

to a compound of the formula I.

The dehydration of the starting material may for example be done by means of treatment with sulpuric acid and heating of the reacting mixture. The dehydration of the starting material may also be done by means of other types of acid-catalysis, such as by means of hydrochloric acid, HCl, phosphoric acid, $H_3PO_4$, potassium hydrogen sulphate, $KHSO_4$, or oxalic acid $(COOH)_2$. Other methods for the dehydration of the starting material to form a compound of the formula I are dehydration using phosphoroxichloride $POCl_3$ in pyridine, and dehydration with thionylchloride, $SOCl_2$, in pyridine. Also catalytic dehydration of the starting material may be used. The dehydration is in this case carried out at a temperature of about 300° to 500° C. using a catalyst such as kaolin, alumina or aluminium oxide.

B. Demethylation of a compound of the formula

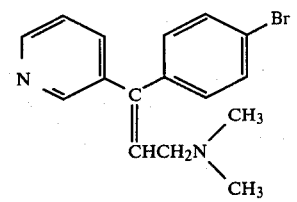

to form a compound of the formula I.

C. Alkylation of monomethylamine with a compound of the formula

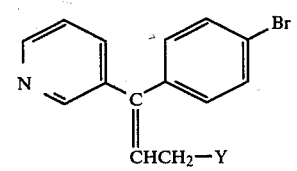

wherein Y is a splittable group to form a compound of the formula I.

Illustrative examples of Y are halogens such as Cl, Br and I or sulphonates such as methanesulphonate, toluenesulphonate and benzene-sulphonate.

D. Introduction of a methyl group into a compound of the formula

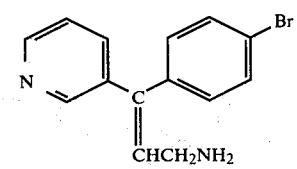

to a compound of the formula I.

E. Treatment under hydrolytic conditions of an acyl or sulphonyl compound of the formula

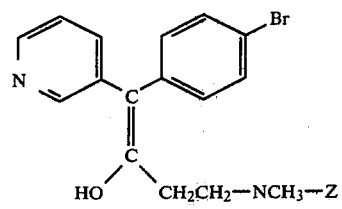

wherein Z is an acyl or sulphonyl group to form a compound of the formula I either directly or via an intermediate of the formula

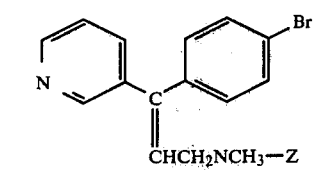

Illustrative examples of Z are acetyl, benzoyl, methanesulphonyl, benzoylmethanesulphonyl and toluenesulphonyl.

(e) Intermediates

For the preparation of the compounds of formula I it has been found that certain hitherto unknown compounds may be valuable.

When preparing the compounds of formula I according to process A, the compound

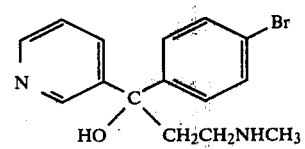

is used as starting material.

This starting material can be prepared according to the reaction scheme

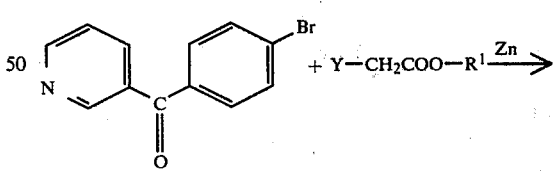

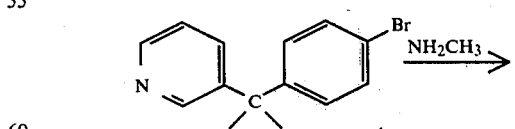

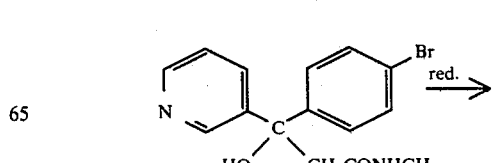

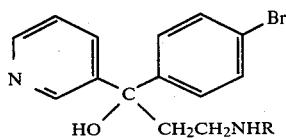

In the reaction scheme Y has the previously given definition and $R^1$ is a lower alkyl group with 1–5 carbon atoms, preferably an ethyl group. The reduction in the last step is preferably carried out with a hydride reagent.

When preparing the compound of the formula I according to process C compounds of the formula

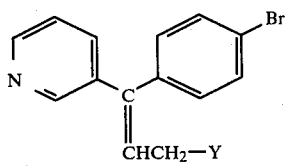

wherein Y is a splittable group are used as starting material.

This starting material can be prepared according to the reaction scheme

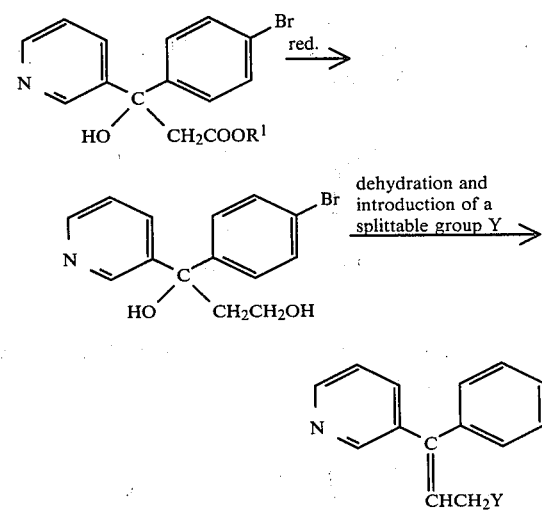

In the reaction scheme above Y and $R^1$ have the previously given definition. The reduction in the first step is preferably carried out using LiAlH$_4$. The last step is preferably accomplished using PBr$_3$, which means that the splittable group Y is Br.

The same starting material in which the splittable group is a halogen may also be obtained by the following reaction scheme:

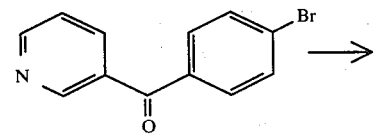

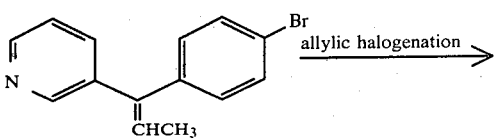

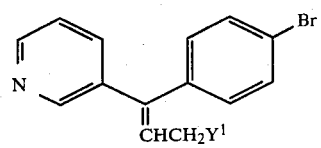

wherein Y' is a halogen such as Cl, Br or I. The allylic halogenation is carried out with a suitable halogenating agent such as a halogen succinimide.

When preparing the compound of the invention according to process D a compound of the formula

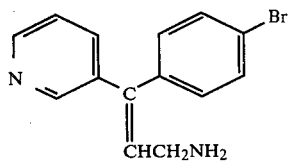

is used as starting material. This compound may be prepared according to methods similar to methods A, B, C and E described in paragraph (d).

Still further methods exist for the preparation of the starting material, for instance according to the reaction scheme:

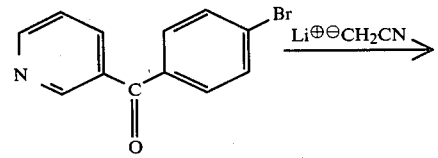

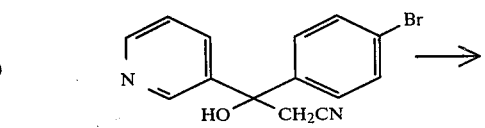

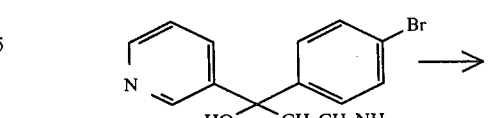

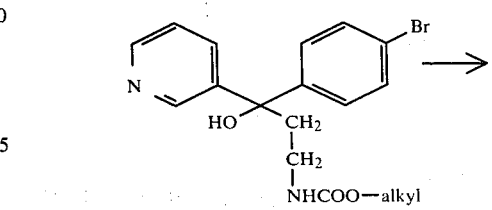

-continued

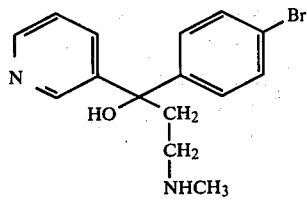

(f) Working Examples
Preparation of Intermediates
Example A

Step 1

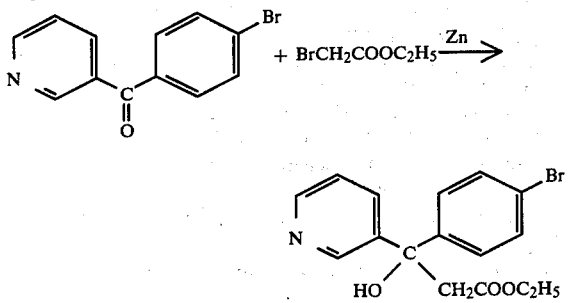

A mixture of 4-bromophenyl-3-pyridylketone [CA 66, 37125^h (1967); 50 g, 0.19 moles] and activated zinc (20 g) in benzene (100 ml) was heated to reflux. Ethyl bromoacetate (56 g, 0.35 moles) dissolved in benzene (50 ml) was added carefully during 30 minutes. Another portion of zinc (50 g) was added and the mixture was refluxed for 14 hours. After cooling and filtration, benzene (300 ml) was added to the filtrate, which was washed three times with 10% aqueous acetic acid solution.

Ethyl ether (200 ml) was added and the solution acidified with 10% hydrochloric acid. The precipitate was filtered off, washed with ether and dried. Yield: 75%. M.p. 168°–175° C.

Step 2

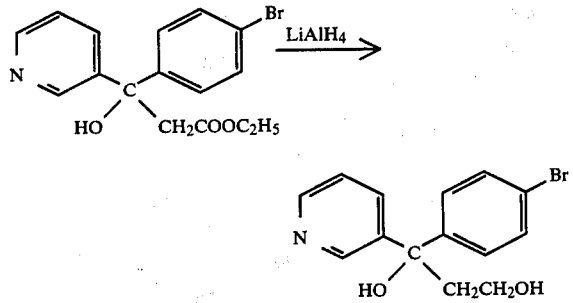

The base (9.5 g, 0.027 moles) from ethyl 3-(4-bromophenyl)-3-hydroxy-3-(3-pyridyl)propanoate hydrochloride (step 1) was prepared and dissolved in ethyl ether (50 ml). This solution was added dropwise to an ice-cold mixture of lithium aluminum hydride (1.0 g, 0.027 moles) and ethyl ether (150 ml). The reaction mixture was refluxed for 5 hours, cooled and a saturated sodium sulphate solution was added until a white precipitate was formed. This was filtered off and the filtrate evaporated. The residue was crystallized from chloroform.

1-(4-bromophenyl)-1-(3-pyridyl)-1,3-propanediol was obtained. Yield: 39%. M.p. 130°–132° C.

Example B

Step 1

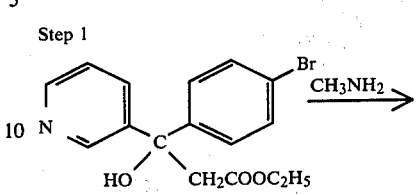

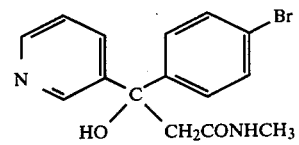

3-(4-bromophenyl)-3-hydroxy-N-methyl-3-(3-pyridyl)-propionamide 19.4 g (0.05 mole) of ethyl 3-(4-bromophenyl)-3-hydroxy-3-(3-pyridyl)-propanoate, 200 ml of 40% solution of methylamine in water and 30 ml of absolute ethanol was stirred for 24 hours at room temperature. The precipitate was filtered off and recrystallized from isopropyl alcohol, which gave 13.2 g (79%) of the amide. M.p. 188°–191° C. The formula $C_{15}H_{15}BrN_2O_2$ was verified through elemental analysis. (The elemental analyses throughout this application were carried out for all elements of the compounds prepared, and are within ±0.4 percent of the theoretical values if not otherwise stated.)

Step 2

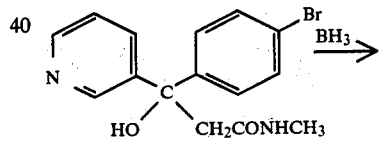

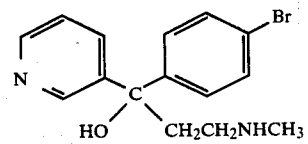

3-(4-bromophenyl)-3-hydroxy-N-methyl-3-(pyridyl)-propylamine

To 1.0 g (3.1 mmole) of 3-(4-bromophenyl)-3-hydroxy-N-methyl-3-(3-pyridyl)-propionamide and 0.8 g (0.02 mole) of sodium borohydride in 60 ml of dry tetrahydrofuran at 0° and under $N_2$, was added dropwise over 20 minutes 4.6 (0.03 mole) of boron trifluoride ethyl etherate in 20 ml of dry tetrahydrofuran. The mixture was stirred over night at room temperature, and then cautiously hydrolyzed with water. Alkalization with 2 M NaOH and extraction with ether gave after evaporation 0.9 of a semicrystalline residue. Recrystallization from ether petroleum ether gave 0.2 g (23%) of the amine. M.p. 81°–88° C.

Example C

Step 1

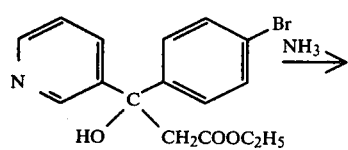

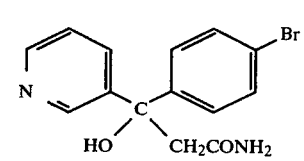

3-(4-bromophenyl)-3-hydroxy-3-(3-pyridyl)-propionamide 0.8 g (2.5 mmole) of ethyl 3-(4-bromophenyl)-3-hydroxy-3-(3-pyridyl)-propanoate, 50 ml of aqueous ammonia and 10 ml of absolute ethanol was stirred at room temperature for 24 hours. The white precipitate obtained was collected by filtration. Recrystallization from isopropyl alcohol gave 0.45 g (56%), m.p. 213°–214° C. The formula $C_{14}H_{13}BrN_2O_2$ was verified through elemental analysis, C calculated 52.4, found 51.9.

Step 2

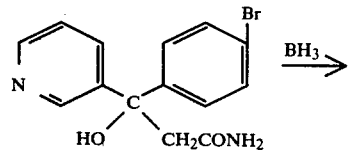

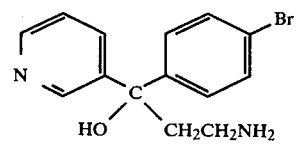

3-(4-bromophenyl)-3-hydroxy-3-(3-pyridyl)-propylamine

To 1.0 g (3.1 mmole) of 3-(4-bromophenyl)-3-hydroxy-3-(3-pyridyl)-propionamide and 0.8 g (0.02 mole) of sodium borohydride in 60 ml of dry tetrahydrofuran at 0° C. and under $N_2$, was added dropwise over 20 minutes 4.6 g (0.03 mole) of boron trifluoride ethyl etherate in 20 ml of dry tetrahydrofuran. The mixture was stirred for 48 hours at room temperature, and then cautiously hydrolyzed with water. Alkalization with 2 M NaOH and extraction with ether gave after evaporation a semi-crystalline residue. Recrystallization from ether-petroleum ether gave 0.6 g (63%) of the amine, m.p. 95°–115° C. NMR-spectrum ($COCl_3$): $2H(2.4, 1\text{-}CH_2)_m$: $2H(3.0, 2\text{-}CH_2)_m$: $3H(3.6, -OH, -NH_2)_b$: $6H(7.1-8.0\ ArH)_m$: $2H(8.6)_m$ Step 3

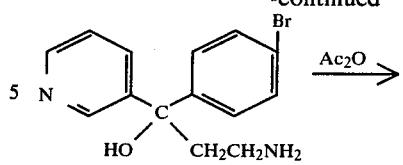

3-(4-bromophenyl)-3-(3-pyridyl)-allylamine

The raw product of 3-(4-bromophenyl)-3-hydroxy-3(3-pyridyl)-propylamine (from 0.4 g of 3-(4-bromophenyl)-3-hydroxy-3-pyridyl)-propionamide) was added with stirring to 50 ml of acetic anhydride and 0.25 ml of concentrated sulphuric acid and the mixture was heated at 130° for 45 minutes. The mixture was then cooled, poured onto crushed ice, alcalized with 30% NaOH and extracted with ether. Evaporation gave 0.36 g of an oil. After hydrolysis with 15 ml of concentrated hydrochloric acid for four hours 0.25 g of an oil was obtained. Thin layer cromatography showed two spots with $R_f=0.1$ and 0.8. Column chromatography on Silica Gel with methanol as eluant gave 0.06 g of the faster moving fraction and 0.19 g of the slower one, which was the amine. The oxalate of this compound was prepared. It was recrystallized from ethanol, M.p. 153.5°–155.5° C.

The NMR spectrum shows the vinyl proton as a double triplet at 6.1–6.5 ppm indicating an isomer ratio 1:1. The formula: $C_{14}H_{13}BrN_2 \cdot 1\ H_2O$ was verified through elemental analysis.

The oxalate was further recrystallized from a mixture of equal volumes of methanol and isopropyl alcohol and once from pure methanol. A substance melting at 160°–162° C. was obtained. The NMR spectrum showed it to be the Z isomer.

Eample D

Step 1

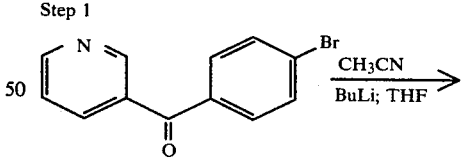

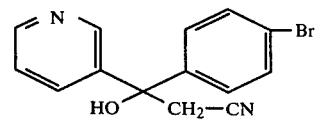

3-(4-bromophenyl)-3-hydroxy-3-(3-pyridyl)-propionitrile

A mixture of 6.5 g (0.16 mole) of acetonitrile and 50 ml of dry tetrahydrofuran (THF) was slowly added under $N_2$-atm to a mixture of 100 ml of 1.5 M n-buthyllithium in hexane and 50 ml of dry THF at $-50°$ C. After stirring for 35 minutes a solution of 36.5 g (0.14 mole) of 4-bromophenyl-3-pyridylketone in 250 ml of dry THF was added at −50° C. The temperature was kept at −70° C. for 15 minutes, then the reaction mixture became viscous and it was allowed to reach ambient temperature. The product was poured into a stirred mixture of 500 g of icewater and 500 ml of methylene chloride. The layers were separated and the aqueous layer was extracted with 2×200 ml of CH₂Cl₂. The combined organic layers were washed with water and dried. The solvent was evaporated giving 39.7 g of an oil. It was dissolved in 550 ml of hot i-PrOH and a solution of 35 ml of 4M HCl-ether (0.14 mole) in 100 ml of i-PrOH was added. After cooling there was collected 34.6 g (74%) of the hydrochloride of 3-(4-bromophenyl)-3-hydroxy-3-(3-pyridyl)-propionitrile. M.p. 158°–161° C.

Step 2

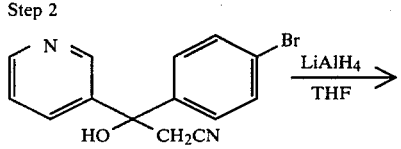

3-(4-bromophenyl-3-hydroxy-3-(3-pyridyl)-propylamine 17.2 g (0.056 mole) of 3-(4-bromophenyl)-3-hydroxy-3-(3-pyridyl)-propionitrile was dissolved in 175 ml of THF and diluted with 200 ml of ether. The solution was cooled to −35° C. and 4.0 g (0.112 mole) of LiAlH₄ was added in portions under N₂-atm. The mixture was held at 0° C. for 2 hours then at 15° C. for 2 hours. 20 ml of a solution of saturated Na₂SO₄ was slowly added. After 30 minutes the mixture was filtered and the inorganic salts were washed with 2×100 ml of ether. The filtrate was collected and the solvent was evaporated giving 14.7 g of an oil. It was diluted with 500 ml of hot i-PrOH and 4.3 g (0.048 mole) of oxalic acid in 300 ml of hot i-PrOH was dropwise added. After cooling over night 11.8 g of crystals, m.p. 98°–105° C. were collected. An analytical sample of the free amine had m.p. 118°–120° C. from i-PrOH. Yield 51%.

Step 3

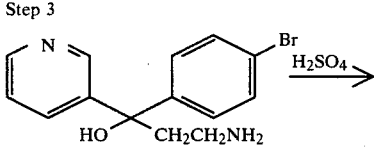

3-(4-bromophenyl)-3-(3-pyridyl)-allylamine

To 0.80 g (0.002 mole) of the oxalate of 3-(4-bromophenyl)-3-hydroxy-3-(3-pyridyl)-propylamine was added 6 ml of 70% H₂SO₄ for 35 minutes. Ice-water was added, then 30 ml of 30% NaOH and the mixture was extracted with 3×100 ml of ether. Drying and evaporation of the solvent gave 0.62 g of an oil. This was dissolved in 10 ml of hot ethanol and a hot solution of 0.20 g of oxalic acid in 5 ml of ethanol was added. Upon cooling 0.49 g of crystals were collected. NMR showed the product to be a mixture of E and Z isomers of 3-(4-bromophenyl)-3-(3-pyridyl)-allylamine as in Example C step 3.

Preparation of the End Product

EXAMPLE 1, (Method C)

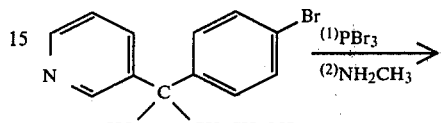

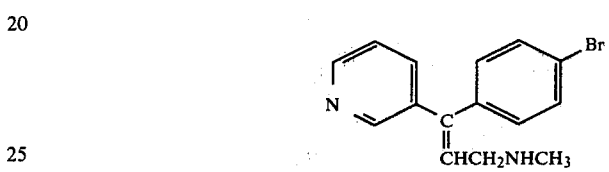

1-(4-bromophenyl)-1-(3-pyridyl)-1,3-propanediol (prepared in accordance with Example A, 7.2 g, 0.023 moles) was dissolved in dry acetone (70 ml). Hydrogen bromide was bubbled through the solution and the solvent was removed in vacuum. Methylene chloride (50 ml) and phosphorus tribromide (6.4 g, 0.047 mole) were added to the residue and the mixture was refluxed for 14 hours, poured into ice and made alkaline with sodium carbonate. Methanol (50 ml) was added to the organic phase and the solution was evaporated in vacuum at 30° C. to 30 ml. The solution was heated with monomethylamine (14 g, 0.47 mole) in an autoclave at 110° C. for 15 hours. After cooling, the solvent was evaporated and the residue was dissolved in ether (25 ml) and water (25 ml). The pH of the mixture was adjusted to 9.0 with ammonia and the layers were separated. Another portion of water was added to the etheral layer and pH was adjusted to 2.1 with HCl. The water-phase was treated with carbon black and then made alkaline with ammonia and extracted with ether. The organic-phase was dried with sodium sulphate and evaporated in vacuum. The residual base was dissolved in ether (40 ml) and cooled on an ice bath. Hydrochloric acid in ether was added dropwise whereupon a slightly yellow precipitate was obtained. The precipitate was filtered off, washed with ether and dried in vacuum. The hydrochloride of 3-(4-bromophenyl)-N-methyl-3-(3-pyridyl)-allylamine was obtained. Yield: 43%. M.p. 138°–144° C.

EXAMPLE 2 (Method A)

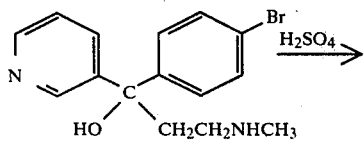

-continued

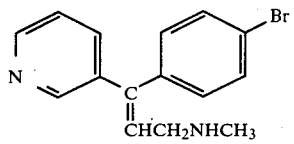

The raw product of 3-(4-bromophenyl)-3-hydroxy-N-methyl-3-(3-pyridyl)-propylamine (prepared in accordance with Example B from 5.0 g of 3-(4-bromophenyl)-3-hydroxy-N-methyl-3-pyridyl)-propionamide) was added with stirring to 50% sulphuric acid (50 ml) and the mixture was heated at 110° for 10 minutes. The mixture was then cooled, poured on to crushed ice, made basic by the addition of 30% NaOH and extracted with ether. Evaporation gave 4.9 g of semicrystalline residue. 150 ml acetone was added and the solution was clarified by filtration. 0.9 g (0.1 mole) of oxalic acid dissolved in 25 ml of acetone was added dropwise to the filtrate. The white precipitate was collected and recrystallized from 350 ml isopropyl alcohol to yield 1.7 g of white crystals of the oxalate of 3-(4-bromophenyl)-N-methyl-3-(3-pyridyl)-allylamine. M.p. 180°–208° C. The NMR spectrum shows the vinyl proton as a double triplet at 6.1–6.4 ppm, indicating a mixture of E and Z isomers.

Isolation of the Z-isomer: After recrystallization three times from ethanol 0.5 g substance was obtained. M.p. 202°–205° C. The NMR spectrum shows the vinyl proton as a single triplet with J=3.4 Hz and in a position which indicates that the compound is the Z-isomer.

The amine oxalate obtained was converted into the corresponding hydrochloride via the free base. Recrystallization from acetonitrile containing a few percent of water gave a compound melting at 161°–165° C. Elemental analysis showed it to be a dihydrochloride with the composition $C_{15}H_{15}BrN_2 \cdot 2HCl \cdot H_2O$.

Isolation of the E-isomer: Mother liquors from the isolation of the Z isomer, containing both isomers in a ratio of about 60:40 E and Z respectively, was used. The oxalate of this amine mixture was recrystallized three times from acetonitrile containing 15% of water, giving a substance melting at 198°–201° C. According to the NMR spectrum this substance was the E isomer.

(g) Pharmacological Tests

It is not possible by experimental means to induce depressions in laboratory animals. In order to evaluate a possible anti-depressive effect of new substances biochemical-pharmacological test methods must be resorted to. One such method, which seems to give a good indication of the potential anti-depressive effects of the test substances, is described in Europ. J. Pharmacol. 17, 107, 1972.

This method involves the measurement of the decrease in the uptake of $^{14}C$-5-hydroxytryptamine ($^{14}C$-5-Ht) and $^3H$-noradrenaline ($^3H$-NA) in brain slices from mice after in vivo and in vitro administration of the test substance.

Inhibition of the uptake of $^{14}C$-5-HT and $^3H$-NA in vitro and in vivo

The test substances were administered intraperitoneally half an hour before the animals were killed. The midbrain was taken out, sliced and incubated in a mixture consisting of 0.2 nmole of $^{14}C$-5-HT, 0.2 nmole of $^3H$-NA and 11 µmole of glucose in 2 ml of Krebs-Henseleit buffer, pH 7.4 per 100 mg of brain slices. The incubation time was 5 minutes with 5 minutes of preincubation before the labelled amines were added. The slices were dissolved in Soluene ® and the amounts of radio-active amines taken up were determined by liquid scintillation. The doses producing 50 percent decrease of the active uptake ($ED_{50}$) of $^{14}C$-5-HT and $^3H$-NA were determined graphically from dose response curves. Active uptake is defined as that part of the radioactive uptake which is inhibited by a high concentration of cocaine.

In the in vitro method, slices of mouse midbrain were preincubated for 5 minutes with a solution of the compound to be tested and then incubated as described above.

TABLE

Inhibition of neuronal uptake of 5-hydroxytryptamine and noradrenaline in slices from mouse brain

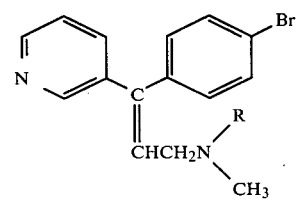

| | Compound R | isomer | salt | Uptake of $^{14}C$-5-HT in vitro $EC_{50}$ µM | in vivo $ED_{50}$ µmole/kg i.p. | Uptake of $^3H$—NA in vitro $EC_{50}$ µM | in vivo $ED_{50}$ µmole/kg i.p. |
|---|---|---|---|---|---|---|---|
| | H | mixture | oxalate | 0.5 | 32 | —(1) | —(1) |
| Compounds of the invention | H | Z | oxalate | 0.5 | 18 | 2.5 | 102 |
| | H | Z | hydrochloride | 0.1 | 15.2 | 1.5 | >101(2) |
| | H | E | oxalate | 2.5 | 102 | 0.8 | 25 |
| Prior art compounds | $CH_3$ | Z | hydrochloride | 1.7 | 49 | 24.4 | >98 |
| | $CH_3$ | E | oxalate | 6.1 | >98 | 6.1 | 25 |
| | imipramine | | hydrochloride | 0.3 | 125 | 0.08 | 63 |

(1) not tested
(2) 38% inhibition recorded at the dose 101 µmole/kg i.p.

As can be seen from the Table the compounds of the invention are potent inhibitors of the neuronal uptake of 5-hydroxytryptamine and noradrenaline. The Z-form of the compound of the invention shows a stronger inhibition of the uptake of 5-HT in vivo than do any of the prior art compounds tested.

The Z-form of the compound of the invention tested as the hydrochloride, is further a more potent inhibitor of the uptake of 5-HT in vitro than any of the prior art compounds. (The difference appearing between the oxalate and the hydrochloride is believed to be due to the fact that the hydrochloride was prepared from the oxalate whereby a more pure Z-isomer was obtained). The E-form of the compound of the invention primarily inhibits the uptake of noradrenaline. The inhibition of neuronal uptake of 5-hydroxytryptamine and noradrenaline disclosed, may give the compounds of the invention value as anti-depressive agents. Likewise the compounds of the invention may be useful as anxiolytic agents.

We claim:

1. A pharmaceutical composition which comprises as active ingredient a therapeutically effective amount for the treatment of depression of a compound of the formula

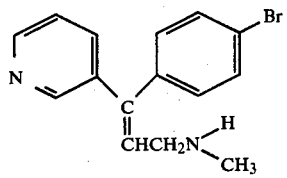

or a pharmaceutically acceptable salt thereof, in association with a pharmaceutically acceptable carrier.

2. A method for the treatment of depressions, characterized in administration to a host suffering from such ailment a therapeutically effective amount of a compound of the formula

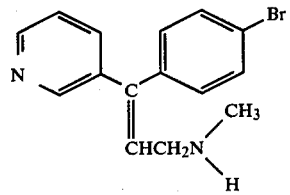

or a pharmaceutically acceptable salt thereof.

3. A method for the treatment of anxiety, characterized in administration to a host suffering from such ailment a therapeutically effective amount of a compound of the formula

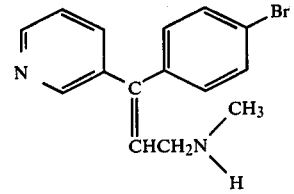

or a pharmaceutically acceptable salt thereof.

4. A compound having the formula

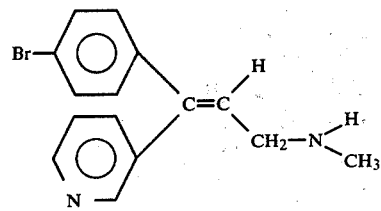

and having a melting point range between about 202° C. to about 205° C. as the oxalate salt, or a pharmaceutically acceptable acid addition salt thereof.

5. A compound having the formula

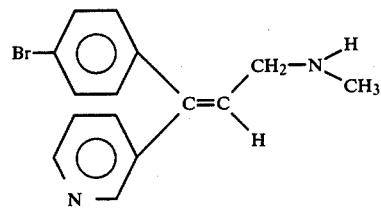

and having a melting point range between about 198° C. to about 201° C. as the oxalate salt, or a pharmaceutically acceptable acid addition salt thereof.

6. A pharmaceutical composition which comprises as an active ingredient a therapeutically effective amount for the treatment of depression of a compound of the formula

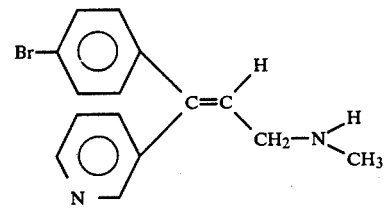

or a pharmaceutically acceptable salt thereof, in association with a pharmaceutically acceptable carrier.

7. A pharmaceutical composition which comprises as an active ingredient a therapeutically effective amount for the treatment of depression of a compound of the formula

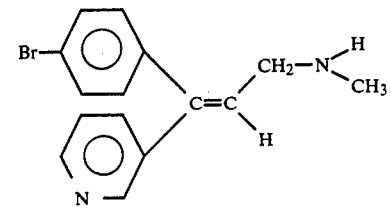

or a pharmaceutically acceptable salt thereof, in association with a pharmaceutically acceptable carrier.

8. A method for treatment of depression characterized by administration to a host suffering from such ailment of a therapeutically effective amount of a compound of the formula

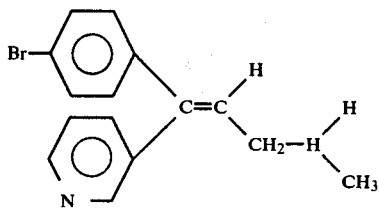

or a pharmaceutically acceptable salt thereof.

9. A method for treatment of depression characterized by administration to a host suffering from such ailment of a therapeutically effective amount of a compound of the formula

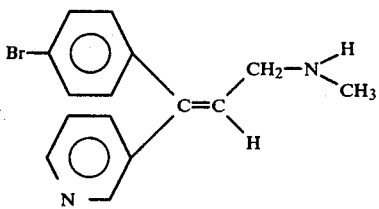

or a pharmaceutically acceptable salt thereof.

10. A method for the treatment of anxiety characterized by administration to a host suffering from such ailment of a therapeutically effective amount of the compound of the formula

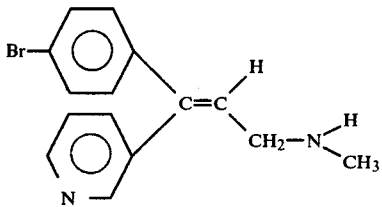

or a pharmaceutically acceptable salt thereof.

11. A method for the treatment of anxiety characterized by administration to a host suffering from such ailment of a therapeutically effective amount of the compound of the formula

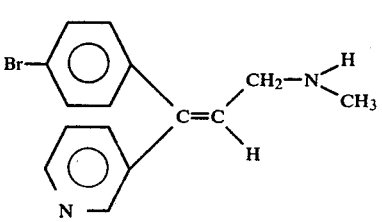

or a pharmaceutically acceptable salt thereof.

* * * * *

UNITED STATES PATENT OFFICE
CERTIFICATE OF CORRECTION

Patent No. 4,186,202　　　　　　　　Dated January 29, 1980

Inventor(s)　Per Arvid Emil Carlsson et al.

It is certified that error appears in the above-identified patent and that said Letters Patent are hereby corrected as shown below:

Page 1, Item [75], line 2, "Vante" should read --Svante--.

Signed and Sealed this

Third Day of June 1980

[SEAL]

Attest:

SIDNEY A. DIAMOND

Attesting Officer　　　Commissioner of Patents and Trademarks